United States Patent [19]
Evans, Jr. et al.

[11] Patent Number: 5,639,451
[45] Date of Patent: Jun. 17, 1997

[54] HAIR TREATMENT COMPOSITIONS

[75] Inventors: Roy M. Evans, Jr., 77 Waring Rd., Memphis, Tenn. 38117; Edward R. Moore, Coon Rapids, Minn.

[73] Assignee: Roy M. Evans, Jr., Memphis, Tenn.

[21] Appl. No.: 476,453

[22] Filed: Jun. 7, 1995

[51] Int. Cl.$^6$ ................................ A61K 7/06; A61K 7/09
[52] U.S. Cl. ........................ 424/70.51; 424/70.13; 132/204
[58] Field of Search ...................... 424/70.51, 70.5, 424/70.2, 70.13; 132/204

[56] References Cited

U.S. PATENT DOCUMENTS

| | | | |
|---|---|---|---|
| 2,115,156 | 4/1938 | Brown | 167/87.1 |
| 3,142,623 | 7/1964 | Zviak | 424/70.51 |
| 4,426,376 | 1/1984 | Shirakura et al. | 424/71 |
| 4,795,629 | 1/1989 | Siuta-Mangano | 424/70 |
| 4,947,878 | 8/1990 | Crews et al. | 132/203 |
| 5,101,841 | 4/1992 | Crews et al. | 132/203 |
| 5,165,427 | 11/1992 | Borish | 132/204 |
| 5,200,175 | 4/1993 | Tabata | 424/70.51 |
| 5,208,014 | 5/1993 | Dubief | 424/70.51 |
| 5,223,252 | 6/1993 | Kolc et al. | 424/72 |
| 5,260,054 | 11/1993 | Nandagiri et al. | 424/71 |
| 5,332,570 | 7/1994 | Bergstrom | 424/72 |
| 5,415,856 | 5/1995 | Crews et al. | 424/70.2 |

FOREIGN PATENT DOCUMENTS

| | | | |
|---|---|---|---|
| 0299764A2 | 1/1989 | European Pat. Off. | A61K 7/09 |
| 3631991A1 | 3/1988 | Germany | A61K 7/09 |
| 5762217A | 4/1982 | Japan | A61K 7/09 |
| 63146808 | 6/1988 | Japan | A61K 7/09 |
| 253714A | 8/1988 | Japan | A61K 7/09 |

OTHER PUBLICATIONS

F.E. Wall, "Hair Straighteners," *Cosmetics: Science and Technology*, vol. 2, 2nd ed., John Wiley & Sons, p. 265 (1972).

CA Selects: Cosmetic Chemcials, Issue 1, 1989, 109:236730h.

C. Zviak, "The Science of Hair Care, Permanent Waving and Hair Straightening," p. 191 (1986).

M.G. DeNavarre, "Chemistry and Manufacture of Cosmetics," Chapter 26, D. Van Nostrand Company, Inc., pp. 443–485.

H. Nuroff and R.L. Hill, "The Proteins vol. 4," Third Edition, Chapter 1 (1979).

F. Lewis, M.D., *Journal of the American Medical Assoc.*, p. 36, Jan. 7, 1939.

*Primary Examiner*—Sallie M. Gardner
*Attorney, Agent, or Firm*—Synnestvedt & Lechner

[57] ABSTRACT

Disclosed are methods and compositions for the treatment of hair. Treating compositions comprising cysteine and/or another active shaping compound, cysteamine and a non-reducing disaccharide are disclosed. The methods of the present invention comprise application of the composition to the hair for permanently altering the natural shape of the hair.

10 Claims, No Drawings

HAIR TREATMENT COMPOSITIONS

RELATED APPLICATIONS

The present application is related by subject matter to U.S. Pat. No. 4,947,878, issued Aug. 14, 1990, U.S. Pat. No. 5,101,841, issued Apr. 7, 1992, and U.S. Pat. No. 5,415,856, issued May 16, 1995, the contents of all of which are incorporated herein by reference.

FIELD OF THE INVENTION

The present invention relates to methods and compositions for the treatment of hair, and more particularly to methods and compositions for permanently altering the shape of hair.

BACKGROUND OF THE INVENTION

The treatment of human hair to alter its appearance, including its color and shape, has long been an objective of the hair care industry. In order for such treatments to be considered successful, especially for treatments in vivo, varied and sometimes contradictory requirements must be satisfied. For example, the capability of precisely producing the desired degree of shape alteration is of primary importance for all hair perming and straightening techniques. However, the ability to fully achieve this objective has heretofore frequently been limited by countervailing requirements. For example, treatments must be effectively completed in the shortest possible period of time in order to be acceptable to the person undergoing the treatment; yet, longer treatment times have heretofore sometimes been required to achieve the desired degree of shape alteration. On the other hand, longer treatment times tend to produce hair damage and offensive skin and/or scalp irritation.

It has heretofore been common practice to treat kinky or curly hair with highly alkaline or caustic aqueous solutions in an effort to soften or reduce the natural elasticity or resiliency of the hair. While the use of such solutions has been partially effective, there are many serious disadvantages as well. For example, methods employing such compositions usually require that the hair and scalp be exposed to highly caustic conditions (e.g.: pH of about 12 to 14) for extended periods of time (e.g.: 45 minutes). Such exposure has heretofore frequently caused a permanent deleterious effect on the aesthetic and structural qualities of the hair and has been known to frequently cause severe irritation or burning of the scalp. See, for example, the article by F. Lewis, M. D., in the Journal of the American Medical Association, Jan. 7, 1939. Moreover, such compositions usually have a very unpleasant odor and are uncomfortable to the person whose hair is being treated. Moreover, it is difficult or impossible to alleviate such offensive odors by traditional methods, such as including a pleasant fragrancing agent in the solution since the compounds of the fragrance are usually destroyed or rendered ineffective in highly caustic solutions. It also appears that such compositions have heretofore caused changes in the structure of the hair which preclude further beneficial chemical treatment of the hair, such as coloring. For example, hair treatment compositions containing sodium or potassium hydroxide, especially at high concentrations of active ingredient, can cause rupture of various linkages and bonds in the protein molecules of the hair to an extent that damage to and embrittlement of the hair occur. For this reason, all heretofore used compositions of this type have required the use of a protective cream which is applied to the scalp and surrounding epidermis prior to application of the shape altering composition. See Wall, F. E., "Hair Straighteners," *Cosmetics: Science and Technology*, Vol. 2, 2nd ed., John Wiley & Sons, p. 265 (1972).

Methods are also currently available for imparting a so-called "permanent wave" to hair which is naturally relatively straight. One frequently used method requires application of a highly alkaline solution to the hair and subsequent physical curling of the hair in the presence of heat. See for example U.S. Pat. No. 2,115,156—Brown. In addition to the disadvantages described above in connection with the use of highly caustic solutions, another problem with such methods is that they require the use of high heat in close proximity to the skin and scalp, creating the potential for severe burning.

Methods also exist for imparting a permanent wave to hair without the application of heat. Such methods generally require the application of a highly alkaline softening composition to the hair, followed by mechanically conforming the hair to the desired shape. An acidic fixing composition is then applied directly to the conformed and softened hair. The fixing composition neutralizes the softening composition and is said to restore the natural elasticity to the hair. An example of such a method is described in U.S. Pat. No. 2,061,709—Malone. Once again, these methods suffer from all the disadvantages associated with the application of a highly caustic composition to the hair. Moreover, it is difficult if not impossible, to apply the exact amount of acidic fixing composition required to completely neutralize the softening composition without leaving the hair in a slightly acid condition, which in turn will result in an undesirable further softening of the hair.

Another method which has heretofore been used for the treatment of hair includes mixing cysteine in powder or crystalline form to a treating solution just prior to application of the solution to the hair. The treating solution of such heretofore used methods generally comprised sodium hydroxide solutions having a pH of about 12. Of course, such caustic solutions suffer from all the disadvantages described above, such as the scalp burning and hair damage which may result from the use thereof. Moreover and just as importantly, cysteine is unstable in aqueous solution and is readily oxidized by dissolved oxygen, thereby precluding long-term storage of the heretofore used solutions. Another disadvantage is that such methods are cumbersome, inconvenient and may result in an improperly formulated treating solution. It also is relatively expensive to separately and anaerobically package an accurately defined amount of cysteine powder, as would be required to prevent oxidation or decomposition.

More recently, as disclosed in above-listed U.S. Pat. Nos. 4,947,878, 5,101,841 and 5,415,856, it has been found that safe, effective methods and compositions for the chemical treatment of hair, and, more particularly, for imparting a permanent wave to hair without the application of substantial heat thereto, or for otherwise altering the configuration of hair while protecting the hair and scalp from the deleterious effects of exposing the hair to highly caustic solutions, as well as stable aqueous solutions containing cysteine or a similar shaping agent for the treatment of hair, are disclosed that employ a hair shaping composition comprising a shaping agent and a disaccharide. According to preferred embodiments disclosed therein, the shaping agent comprises a reducing agent for reducing the hair. According to other preferred embodiments disclosed therein, the shaping agent comprises alkali. Such compositions have been found to provide excellent ability to cause the desired degree of shape alteration while simultaneously protecting the hair and scalp from burning or damage.

According to certain other preferred embodiments thereof, it was found that certain stabilized solutions of cysteine or other shaping agents are effective softening or reducing agents in the treatment of hair. More particularly, it was found that aqueous solutions containing cysteine or another shaping agent and a non-reducing disaccharide are stable and effective compositions for treating hair.

German Offen. DE 3,631,991, discloses a reducing agent composition that is a combination of cysteamine, or its salts, together with a monothioglycolic acid ester for permanent hair waving (see CA Selects: Cosmetic Chemicals, Issue 1, 1989, 109:236730h). Also, the use of an N-acylcysteamine, HSCH$_2$CH$_2$NH—COR (R-2-10 C alkyl), as a hair reducing compound, together with another reducing agent selected from the group consisting of cysteine, acidic sodium hyposulfite, sodium sulfite, thioglycerol and thiolactic acid is disclosed in Japanese Patent JP 63146808. Also, published European Patent Application 88 306449.5, publication number 0299764, discloses the use of cysteamine as a reducing agent together with sulfite, bisulfite and disulfide compounds, such as cystamine, to effect reoxidation; and the use of cystamine, as an oxidizing agent in the permanent waving process is disclosed in U.S. Pat. No. 4,795,629. Japanese published Patent Application No. 2053-714-A discloses cysteamine together with a dithioglycolate stop action compound.

It has been postulated that the reducing action of mercaptans on keratin is due mostly to the dissociated form of the thiol groups, the thiolate anion. Acid permanent waves sufficiently curl hair at a lower pH compared to alkaline permanents because the waving agents in these permanents have low pKa values and thus exist predominantly in dissociated (thiolate) form at a pH near neutral, or at a slightly acidic pH. Hence, the pKa value shows that some mercaptans are efficient at high pH values while others with a low pKa value and high ionization constant are efficient at lower pH values. For example, it is well known that the alkaline salts of thioglycolic acid, e.g., the ammonium salt of thioglycolic acid (pKa=10.4), have acceptable waving efficiency only if the pH of the solution exceeds 9. See Zviak, Charles, *The Science of Hair Care, Permanent Waving and Hair Straightening*, p. 191, 1986. On the other hand, amides, such as thioglycolamide (pKa=8.4), and esters, such as glycerol thioglycolate (pKa=7.8), give acceptable waving efficiency at neutral and even slightly acid pH.

Japanese published application No. 55-136857 teaches that cysteamine-based permanent waving compositions are more effective with thioglycolic acid reducing agents. U.S. Pat. No. 5,260,054 discloses a cysteamine-based permanent wave composition, without a thioglycolate or thioglycolic acid, in a single formula which can be applied in a single predetermined amount of time to the hair. According to the disclosure of that patent, regardless of the structure of the hair, whether it be damaged or not, the compositions of the '054 patent are capable of being water wrapped or lotion wrapped without the use of a dryer, hair caps or other heat treatment to speed the reducing agent action. However, such prior art cysteamine-based permanent wave compositions, while having many positive attributes, have an unacceptable malodor associated therewith.

SUMMARY OF THE INVENTION

It has now been surprisingly found that the properties of the hair treatment compositions disclosed in U.S. Pat. Nos. 4,947,878, 5,101,841 and 5,415,856, and particularly the speed of action thereof, can be improved, while maintaining the safety characteristics thereof and also avoiding the unacceptable odor heretofore associated with hair care compositions containing cysteamine, by incorporating cysteamine in such hair care compositions. More particularly, the hair care compositions of the present invention comprise (1) an active shaping compound as defined herein, (2) cysteamine, and (3) a disaccharide.

Preferred method aspects of the present invention relate to a process for altering the shape of hair to a predetermined degree comprising (a) applying to the hair a hair shaping composition, said composition comprising (1) an active shaping compound as defined herein, (2) cysteamine, and (3) a disaccharide; and (b) allowing said composition to remain in contact with the hair for a time sufficient to achieve the predetermined degree of shape alteration.

The present invention also provides methods for treating hair comprising applying a stabilized aqueous solution of cysteine or another active shaping compound as defined herein, cysteamine and a disaccharide to the hair, placing the hair in the modified configuration, and thereafter oxidizing the hair while it is still in said modified configuration.

DETAILED DESCRIPTION OF THE INVENTION

In order to more fully understand the compositions and methods of the present invention, it is helpful to understand the basic structure of hair. Hair is a complex organic substance consisting largely of the protein keratin. More specifically, hair is a proteinaceous fiber comprising a bundle of long individual protein molecules which are intertwined with one another and cross linked at various intervals. Each individual protein molecule comprises condensed amino acids in which the acid end of one molecule is condensed with the amino end of the next. The amino acids are alike in that they all contain an acid group and an amino group, but they may not be alike in certain other details of the arrangement of their atoms. Hair protein generally contains from about 5% to about 15% by weight of the amino acid cystine, which has the empirical chemical formula C$_6$H$_{12}$N$_2$O$_4$S$_2$ and generally conforms to the molecular chemical formula given below:

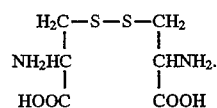

It has been postulated that cystine frequently appears in the fibrous bundle of keratin protein molecules as a bridge between adjacent peptide chains and that it may also frequently appear as a loop or bridge between two segments of the same peptide chain. It is believed that these cystine bridges affect, and in large part determine, the physical shape and conformation of the hair. It has also been postulated that links between adjacent peptide chains may also occur by the ionization of the carboxyl and amino groups to form a salt bridge. Hydrogen bonding is believed to provide a third means by which linkage between adjacent peptide chains may be achieved. It is believed that these additional linkage mechanisms also affect the physical shape and conformation of the hair. See chapter 26 of the book "Chemical and Manufacture of Cosmetics" by Mason G. Denavarre and the first chapter of the book entitled "The Proteins Volume 4", Third Edition, edited by Hans Nuroff and Robert L. Hill, 1979, both which are incorporated herein by reference.

I. The Compositions

The present shaping compositions comprise three important ingredients: (1) from about 5 to about 20% by weight of an active shaping compound, (2) from about 5 to about 20% by weight of cysteamine, and (3) from about 3 to about 20% by weight of a disaccharide, ingredient (1) plus ingredient (2) together comprising from about 10 to about 25% by weight of the total weight of the composition. Applicant has found that the inclusion of cysteamine in compositions according to the teachings of the present invention provides the compositions with highly desirable and unexpected properties. In particular, the compositions of the present invention have been found to be non-damaging to the hair and, at the same time, fast-acting and free of unpleasant odor, a combination of properties not heretofore achieved in such hair care products containing cysteamine. Furthermore, the compositions have also been found to produce shaped hair with exceptional feel and texture and with little or no embrittlement or damage.

A. The Shaping Agents

The compositions of the present invention contain a shaping agent. The term shaping agent is used herein in a non-limiting sense to refer to any agent, compound or composition adapted to permanently alter the shape of hair. Thus, the shaping agents of the present invention include those compositions which tend to straighten naturally curly or kinky hair as well as those which tend to curl naturally straight hair. Furthermore, the term shaping agent is intended to include reducing agents which break cystine disulfide bonds in hair as well as oxidizing agents which establish such disulphide bonds in hair. For the purpose of convenience, shaping compositions which tend to cause breaking of the bonds which contribute to the shape of the hair, such as cysteine disulphide bonds, are sometimes referred to herein as softening compositions. On the other hand, shaping compositions which tend to establish or reestablish such bonds are sometimes referred to herein as fixing compositions.

It is contemplated that the shaping agents of the present invention will generally include one or more active shaping compounds and carrier for the active compounds. It will be appreciated that the terms active shaping compound and carrier are used herein for the purpose of convenience and illustration but not by way of limitation. In particular, the term active shaping compound refers to those components of the shaping agent which interact chemically with the hair to alter the shape of the hair. In contrast, the carrier serves principally to provide the proper environment for the active compounds and to facilitate, enhance and/or modify delivery and application of the active compounds to the hair. The preferred shaping agents of the present invention comprise from about 10 to about 25 percent by weight of active shaping compound plus cysteamine, from about 3 to about 20 weight percent of a disaccharide, and from about 55 to about 87 percent by weight of carrier.

An important aspect of the present invention resides in the weight ratio between the active shaping compound and the other two essential ingredients of the composition: the cysteamine and the disaccharide. Considering first the ratio of disaccharide to active shaping compounds and cysteamine, it is believed that such ratio may vary widely, depending upon numerous factors, such as the type of hair and the degree of shape alteration desired. It is preferred, however, that the weight ratio of the disaccharide to each of the active shaping compound and the cysteamine be from about 0.1:1 to about 4:1. As regards the weight ratio of the active shaping compound and the cysteamine, these are generally between 4:1 and 1:4.

1. Active Shaping Compounds

According to certain embodiments of the present invention, the active shaping compound comprises a reducing compound. As will be appreciated by those skilled in the art, reducing compounds are commonly used as active components for cleaving or breaking the cystine disulphide bonds in hair. Thus, as the term is used herein, reducing compound refers to those compounds which are reducing agents with respect to cystine in the hair. The amount of reducing compound contained in the present compositions will vary widely, depending upon the particular circumstances of each embodiment. It is generally preferred, however, that the present compositions comprises from about 5 to about 20 percent by weight of reducing compound.

The reducing compound to be used in accordance with the present invention may comprise any of a number of reducing compounds conventionally used for the purpose of waving or straightening hair. Generally, it is only required that the reducing compound be nontoxic and free of harmful residue. Thus, the reducing compound of the present invention is preferably selected from the group consisting of sulfites, mercaptans, e.g., thioglycolic acid and the salts thereof, thiolactic acid, monothioglycerol, 1-thioglycerol, 3-mercaptopropionic acid, including cysteine, and mixtures of two or more of the foregoing. Other suitable reducing compounds for use in shaping compositions, in addition to those exemplified above, will be apparent in view of the present disclosure.

According to a presently preferred embodiment of the invention, it is preferred to use cysteine as the active shaping compound for reductively cleaving the sulfur-sulfur bonds of the cystine bridges in hair. It has been found that such cleavage tends to "soften" the hair. As the term is used herein, "softened hair" refers to hair which has been rendered malleable relative to its natural resiliency. In the compositions of the present invention, the active shaping compound, such as cysteine, is believed to cause reductive cleavage of at least a portion of the disulfide bonds within and between the individual protein chains which comprise the hair. The resulting softening of the hair allows the hair to be more readily reconfigured.

Cysteine, 2-amino-3-mercaptopropionic acid, has the empirical chemical formula $C_3H_7NO_2S$ and the molecular chemical formula given below:

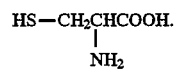

It will be understood that the term cysteine as used herein encompasses within its scope all the various enantiomeric and ionic forms that the cysteine molecule is capable of taking in solution, it being contemplated that all such forms will be capable of performing the desired function. For example, unless otherwise specifically designated herein, the term cysteine includes both L and D enantiomers of that component. It is believed that, up to the solubility limit of cysteine, all concentrations of cysteine in the softening compositions of the present invention will have a degree of effectiveness and therefore all such concentrations are within the broad scope of the present invention. It is preferred, however, that the concentration of cysteine range from about 5 weight percent to about 20 weight percent, and more preferably from about 6 weight percent to about 14 weight percent, depending upon the pH of the solution. For example, when the solution has a pH of between about 8 and about 10, it is preferred that the cysteine concentration range from about 13 weight percent to about 14 weight percent.

According to many preferred embodiments, hair shaping is advantageously carried out under alkaline conditions. Thus, the shaping agent of the present invention preferably includes an alkalizing agent. Such alkalizing agents may be used alone or in combination with the reducing agent or oxidizing agent of the present invention. Alkalizing agents adaptable for use in hair shaping operations are well known in the art, and all such alkalizing agents are within the scope hereof. It is generally preferred, however, that the alkalizing agent of the present invention be selected from the group consisting of hydroxides, carbonates and mixtures of these. Especially preferred are the sodium, potassium and ammonium hydroxides and carbonates.

According to other embodiments of the present invention, the active hair shaping compound comprises an oxidizing compound for creating cross-linkages between adjacent peptide chains of the keratin in the hair, and especially for restoring cystine disulphide bonds in hair. It is contemplated that the types of oxidizing compounds suitable for use in accordance with the present invention are numerous and varied, and all such oxidizing compounds are within the scope hereof. It is generally preferred, however, that the oxidizing compound of the present invention be selected from the group consisting of peroxides, perborates, bromates and mixtures of two or more of the aforementioned. Hydrogen peroxide is an especially preferred oxidizing compound due to its low cost, mild action and ready availability.

It is contemplated that other agents for nonoxidative crosslinking of adjacent peptide chains may also be beneficial in certain embodiments of the present invention. For example, it is contemplated that the shaping agent may comprise a nonoxidative crosslinking agent selected from the group consisting of bivalent metal ions, alkylene dihalides, and aldehydes.

2. The Shaping Agents—Carrier

It will be appreciated by those skilled in the art that many of the active compounds described herein are readily available in the form of solutions or suspensions of one or more liquids, typically aqueous solutions. It is contemplated that the active compounds of the present invention will frequently be utilized in this form, and accordingly the present compositions preferably include a carrier for the active shaping compound. In general it is contemplated that a wide variety of materials will be suitable for use as a carrier, and all such materials are within the scope of the present invention. It is generally preferred that the carrier comprise a liquid, preferably a polar liquid, for facilitating delivery and application of the present shaping agent to the hair. As will be appreciated by those skilled in the art, the physical condition of the carrier may therefore vary widely, ranging, for example, from a thin clear liquid to a creamy paste, depending upon the needs of the particular application.

The carrier of the present invention preferably comprises a solvent for one or more of the active components of the shaping agent. Thus, for compositions containing polar shaping compounds, the carrier preferably comprises a polar liquid, such as water, alcohol and mixtures of these. The term solvent is used in this context in a broad sense to include those liquid components and mixtures of liquid components which have at least some tendency to solubilize at least one active component of the shaping agent. It is especially preferred that the carrier comprise a mixture of water and an alcohol. The composition preferably comprises solvent in an amount from about 55 to about 87 percent by weight of the composition.

According to certain preferred embodiments, such as compositions especially adapted for the straightening of kinky or curly hair, the carrier comprises an oil-in-water emulsion having a continuous water phase and a disperse oil phase. In such embodiments, the active shaping compound is maintained in the form of a solution or suspension in the water phase of the carrier. Such oil-in-water emulsions are preferably relatively highly viscous, creamy materials. These properties and characteristics assist in the application the compositions to the hair. Furthermore, the rheology of these compositions tends to hold the hair in a straightened configuration during processing. Compositions of this type are preferred when the active compound comprises alkali in major proportion. In such embodiments, it is contemplated that the carrier will also include emulsifying agents to aid in the formation and maintenance of such emulsions.

In accordance with a preferred embodiment of the present invention, the carrier comprises a thickening agent for adjusting the rheology of the composition. As the term is used herein, a thickening agent includes any agent which provides a high viscosity to the softening solution thus making it easier to apply. Moreover, the relatively high viscosity imparted by the thickening agent enhances uniform spreading of the treating solution and retards dripping and evaporation of the solution. According to certain embodiments, it is preferred that the thickening agent be water soluble so that it may be readily included in the aqueous solutions of the present invention. The thickening agents suitable for use in the present compositions are those thickening agents typically used in cosmetics and generally include organic and inorganic compounds. Examples of suitable thickening agents include: silica; carboxy alkylcellulose, such as carboxymethylcellulose; fatty alcohols; mineral oils; gelatins; hydroxy alkylcellulose, such as hydroxy ethylcellulose; and mixtures of two or more of these. The concentration of the thickening agents in the compositions of the present invention will vary greatly according to the desired result in each individual case, and, accordingly, all such concentrations are within the scope of the present invention. Applicant has found, however, that thickening agent concentrations of from about 0.5 weight percent to about 2.0 weight percent are preferred for certain embodiments.

The carrier also preferably comprises a detergent and/or conditioner for leaving the hair feeling smooth and soft after treatment with the compositions of the present invention. Suitable detergents include those detergents readily known to those skilled in the hair care art, including primary alkyl sulfates of the $C_{12}$–$C_{18}$ series, salts of oleic acid, ammonium hydroxide, zwitterionic compounds and mixtures of two or more of these. Other detergents suitable for use in the carrier of the aqueous solution of the present invention would be readily apparent based upon the present disclosure.

According to certain preferred embodiments, the compositions of the present invention further include at least one penetrating agent. As the term is used herein, a penetrating agent is any material which improves penetration of the solutions into the hair. Although any penetrating agent heretofore used for the purpose can be used in the present invention as well, particularly preferred penetrating agents are propylene glycol, monoethanolamine, any compound containing an ethoxylate group, and oleth-20, the latter being the generic term for the polyethyleneglycol ether of oleyl or laural alcohol having the formula: $CH_3(CH_2)_7 CH\!=\!CH(CH_2)_7CH_2(OCH_2CH_2)_nOH$, wherein n has an average value of about 20. Oleth-20 is sold under the trade name "BRIJ" by ICI Americas Corp. The concentration of the penetrating agents to be used according to the compositions of the present invention will vary greatly depending upon the amount of penetration desired, and, accordingly, all such concentrations are within the scope of the present invention. Applicant has found that compositions containing a penetrating agent in concentrations from about 4 weight percent to about 10 weight percent are preferred according to certain embodiments.

In certain embodiments, it is preferred that the compositions of the present invention include chelating agents. As the term is used herein, a chelating agent is any polydentate ligand capable of forming a complex with a metal ion. While many such chelating agents are readily available and well known in the art, common chelating agents include amine containing acids, hydroxy carboxylic acids, dicarboxylic acids, alkali metal salts of the foregoing acids, and mixtures of these. It is preferred that the chelating agent comprise hydroxy ethylenediaminetriacetic acid (hereinafter H-EDTA) and even more preferably alkali metal salts of H-EDTA. It is generally preferred that sodium salts of H-EDTA be used as the chelating agents in the compositions of the present invention, and it is even more preferred that trisodium salt of H-EDTA is used as the chelating agent. The inclusion of chelating agents in the compositions of the present invention beneficially removes toxic heavy metals, such as mercury, cadmium, and lead, which otherwise bind to the thio groups of cysteine in the hair protein. Freeing these thio groups is beneficial since the freed thio groups aid in forming the new disulfide linkages after the hair has been reconfigured, thereby helping to maintain the hair in its new configuration. The concentration of the chelating agents in the compositions of the present invention will vary greatly depending upon the circumstances of use in each individual case, and, accordingly, all such concentrations are within the scope of the present invention. Applicant has found however, that chelating agents are preferably included in the compositions of the present invention in concentrations from about 0.25 weight percent to about 1.5 weight percent.

3. The Cysteamine Component

Cysteamine, 2-aminoethyl mercaptan (decarboxycysteine), has the empirical chemical formula $C_2H_7NS$ and the following molecular chemical formula:

In the compositions of the present invention, it behaves as a supplemental shaping agent, providing compositions having faster fixing activity than do similar shaping compositions that do not contain cysteamine. Surprisingly, however, the cysteamine containing shaping compositions of the present invention do not cause the offensive odor associated with previously used shaping compositions that contain cysteamine.

In particular, it has been discovered that when cysteamine is incorporated into the shaping compositions of the present invention, in an amount of from about 5 weight percent to about 20 weight percent of the total composition, the shaping composition has unexpectedly improved shaping properties, particularly with respect to speed of action, without the unpleasant odor heretofore associated with the use of cysteamine in shaping compositions. This is particularly true when the composition comprises a total of from about 10 weight percent to about 25 weight percent of active shaping compound plus cysteamine and from about 3 weight percent to about 20 weight percent of disaccharide.

B. The Disaccharide

An important aspect of the present invention is the provision of hair shaping compositions containing disaccharide. In particular, it is contemplated that the disaccharide of the present invention acts as a protecting agent for protecting the keratin fibers of the hair from undesirable damage and degradation while also permitting, and preferably enhancing, the softening of the hair. Furthermore, applicants have found that the presence of disaccharide in hair treatment compositions tends to also protect the scalp of the person being treated and the hands of the hair care professional from irritation and burning. While applicant does not intend to be bound by or limited to any particular theory, it is believed that the disaccharide provides abundant sites for hydrogen bonding with the molecules which make up the hair. The availability of such sites is believed to compete for the otherwise intermolecular hydrogen bonding which is present among the protein strands. This in turn opens the tertiary or spatial structure of the protein fibers, thereby facilitating reduction of the disulfide, cystine, down the thiol, cysteine. Furthermore, it is believed that the disaccharide component, and preferably sucrose, favorably moderates the oxidative and/or reductive reactions between the active shaping compounds and the components of the hair.

As is well known to those skilled in the art, disaccharides are carbohydrates comprised of two monosaccharide units. As used herein, the term disaccharide refers to all known and available disaccharide compounds, including all stereoisomeric and antiomeric forms thereof. While it is contemplated that all such disaccharides are adaptable for use in the compositions of the present invention, it is highly preferred that the disaccharide comprise, and preferably consist essentially of, a disaccharide which does not contain a "free" aldehyde or ketone group. It is also preferred that the disaccharide of the present invention does not reduce Tollens' or Fehlings' reagent, hereinafter referred to as a "non-reducing disaccharide." Sucrose, which does not contain a free aldehyde or ketone group, is an especially preferred non-reducing disaccharide. Because of its ready availability and low cost, sucrose is especially preferred for use in connection with the compositions of the present invention.

It is contemplated that the amount of disaccharide in the compositions of the present invention, may vary widely, depending upon numerous factors, such as hair type and the desired shape alteration. It is generally preferred, however, as indicated above, that the shaping composition of the present invention comprise from about 3 to about 20 percent by weight of disaccharide.

In accordance with the presently preferred embodiment, the ratios between the shaping compound, preferably cysteine, the cysteamine, and the polysaccharide in the shaping compositions of the present invention may vary widely, depending on the particular application, as long as the foregoing parameters (a minimum of about 5 weight percent of each of cysteine and cysteamine, a total of from about 10 weight percent to about 25 weight percent of cysteine and cysteamine combined, and a total of from about 3 weight percent to about 20 weight percent of polysaccharide), are maintained.

As mentioned above, cysteine is generally very unstable in a solution and is readily oxidized by oxygen which may be dissolved in the solution. This oxidation is manifest in the formation of solid precipitate when an aqueous solution of cysteine is allowed to stand for more than a few hours. Applicant has found that the inclusion of standard antioxidants is generally ineffective for stabilizing aqueous solutions of cysteine. In particular, applicant has found that anti-oxidants such as butylated hydroxy toluene (BHT), ascorbic acid, mercaptans, and hydrogen sulfites are generally ineffective in stabilizing aqueous solutions of cysteine. Importantly and surprisingly, however, applicant has found that the inclusion of a non-reducing disaccharide in an aqueous solution of cysteine stabilize the solution and protects the cysteine from oxidization or other degradation. For example, cysteine solutions containing sucrose according to the present invention have been shown to have at least a one year shelf life.

With respect to embodiments in which the active shaping compound comprises cysteine in major proportion, applicant believes that the inclusion of a non-reducing disaccharide in any measurable concentration in the composition of the present invention will be effective to a degree in stabilizing the softening solution. That is, applicant has found that the concentration of the sucrose impacts the stabilizing effect in degree only and therefore may be varied over a wide range as desired. In particular, those solutions having relatively low concentrations of sucrose will tend to provide a shorter shelf life than those solutions having relatively high sucrose concentrations. Moreover, high concentrations of sucrose in the solution may tend to make the softening composition syrupy and more viscous than is desired in certain embodiments. Accordingly, for embodiments in which the active shaping compound comprises cysteine in major proportion, all concentrations of sucrose are within the scope of the present invention. Applicant has found, however, that in such embodiments the concentration of sucrose preferably ranges from about 3 weight percent to about 20 weight percent, more preferably from about 4 weight percent to about 12 weight percent, and even more preferably from about 4 weight percent to about 8 weight percent. Furthermore, for shaping compositions in which the active shaping compound comprises cysteine in major proportion, the active shaping compound:disaccharide weight ratio is preferably from about 2:1 to about 8:1.

Applicants have found that solutions, preferably aqueous solutions, of cysteine and a non-reducing disaccharide are effective in reductively cleaving the sulfur-sulfur bonds of the cystine bridges in hair, and that such cleavage tends to "soften" the hair. As the term is used herein, "softened hair" refers to hair which has been rendered malleable relative to its natural resiliency. In the compositions of the present invention, cysteine (as well as other active shaping compounds) and cysteamine are believed to cause reductive cleavage of at least a portion of the disulfide bonds within and between the individual protein chains which comprise the hair. This cleavage softens the hair and allows the hair to be more readily reconfigured. Applicant has thus discovered a softening composition, in the form of an aqueous solution, which contains the natural and effective reducing agent cysteine in combination with the rapid acting reducing agent cysteamine and which has no offensive odor, a high degree of stability and a relatively long shelf life. It is believed that the inclusion of non-reductive disaccharides, e.g. sucrose, is an important characteristic of the compositions according to such embodiments of the present invention. Reductive saccharides, such as maltose and lactose, on the other hand, have been found to be generally ineffective, possibly because they compete with the preferred reducing agent of the solution, cysteine. Accordingly, it is preferred that disaccharides which are non-reductive be used in the compositions of the present invention.

For embodiments of the present invention in which the active shaping compound comprises alkali in major proportion, the amount of disaccharide present in the composition is critical to fully achieving the objects of the present invention. In particular, it has been discovered that such compositions, in general, exhibit a gradually increasing effectiveness as the amount of disaccharide in the composition is increased. Surprisingly, however, as the concentration of disaccharide in such compositions approaches 20 percent by weight, a marked decrease in ability to protect the scalp of the user and/or hands of the hair care professional from caustic burning is exhibited. Accordingly, for embodiments in which the active shaping compound comprises alkali in major proportion, it is preferred that the concentration of disaccharide, and preferably non reducing disaccharide, is from about 5 weight percent to about 15 weight percent, more preferably from about 10 weight percent to about 15 weight percent, and even more preferably about 15 weight percent. Furthermore, for shaping compositions in which the active shaping compound comprises alkali, the active shaping compound:disaccharide weight ratio is preferably from about 2:1 to about 10:1.

It is generally preferred that compositions of the present invention comprise an aqueous solution which is not highly caustic. In particular, it is preferred that the pH of the solution be from about 5 to 13 for embodiments in which the active shaping compound comprises cysteine in major proportion. More preferably, the pH is in the range of from about 7 to 11, and even more preferably from about 7.5 to 8.5. Thus, in such preferred embodiments of the present invention, the pH of the reducing composition is high enough to help break the ionic bridges between adjacent protein molecules and thus to enhance the softening capacity of the composition but is low enough to be safe to the scalp and skin. According to one preferred embodiment of the present invention, an alkalizing agent such as ethanolamine is present to adjust the pH of the composition as required. In certain preferred embodiments, ethanolamine is present in a concentration of about 3 weight percent to about 6 weight percent. In the alternative, ammonium hydroxide can be substituted in equivalent amounts for the ethanolamine.

II. The Methods

The present invention also provides methods for modifying the natural conformation of existing hair. As the term is used herein, existing hair refers to fully developed excutaneous hair. As used herein, the term "natural configuration" refers to the configuration of the hair prior to being treated according to the methods of the present invention. That is, the term "natural configuration" is used for convenience only and does not limit the methods of the present invention to treatment of hair which has not been previously treated. Surprisingly and beneficially, the use of the methods and compositions of the present invention provide the capability for effective and non-damaging treatment of previously treated hair. In contrast to the methods and compositions heretofore used, the present invention achieves softening or relaxation of the hair by relatively benign repositioning of the natural constituents of the hair without causing permanent damage thereto. As a result, hair may be subjected to a plurality of treatments without being damaged to any substantial extent.

An important aspect of the methods of the present invention is application of the compositions of the present invention to the hair of the person to be treated. While many methods are known and available to those skilled in the art for the application of softening solutions and those methods may be readily adapted for use with the present compositions, it is preferred that the present compositions be directly applied to the hair. In particular, it is preferred that the application start at the scalp and move progressively outward towards the ends of the hair until the hair being treated is covered thoroughly. It will be understood by those skilled in the art that the particular application method step described above provides unique and substantial advantages over those methods generally used in the prior art. For example, application of the highly alkaline softening compositions heretofore used generally presented a serious risk of caustic burn to both the subject being treated and the person conducting the treatment (hereinafter "the operator"). Accordingly, prior methods require that precautions be taken in order to protect both the user and operator from caustic burn. For example, kits containing such solutions generally include instructions recommending or requiring that the operator wear gloves during the application step and that the skin of the treated person be protected from the solution by thick and highly viscous gels. Due to the relatively benign nature of the present compositions, such cumbersome and inconvenient precautions are not necessary. Moreover, it is imperative according to the heretofore used methods that the application period be strictly controlled and minimized so as to avoid damage to the scalp and hair of the person being treated. Overexposure of the hair to such highly caustic solutions would generally cause severe and irreversible degradation of the structure of the hair. In comparison, the benign nature constituents of the softening solutions according to the present invention eliminates the criticality of the application period and extends the maximum application period nearly indefinitely, especially for embodiments in which the active compound comprises cysteine in major proportion.

As will be appreciated by those skilled in the art, the amount of softening composition to be applied according to the present invention will vary greatly depending upon a host of individual circumstances. For example, the particular type of hair which is to be treated will have a large impact on the amount of composition to be applied. In particular, it is well known that different types of hair have varying degrees of moisture absorbency. Since softening compositions of the present invention preferably comprise an aqueous solution, the ability of the composition to effect hair softening will depend to some extent upon this property of the individual hair. Likewise, the amount of hair to be treated will also determine the application rate of the softening composition. In addition, the extent to which the natural configuration of the hair is to be modified will also impact upon the amount of the composition to be applied. Accordingly, all application rates and amounts are within the scope of the present invention. Applicant has found, however, that based primarily upon considerations of cost and convenience, that the amount of solution to be applied is preferably from about 3 ounces to about 4 ounces and more preferably from about 3.5 ounces to about 4 ounces.

The application period for the compositions of the present invention will also vary widely depending upon a variety of individual circumstances. Importantly and surprisingly, applicant has found that exposure of the hair and scalp to certain compositions of the present invention for extended periods of time will not result in any substantial degradation of the hair or cause deleterious effects to the scalp. On the contrary, it is believed that extended exposure of the hair to the compositions of the present invention, especially those compositions having a pH of about 7, may tend to invigorate and revitalize the hair rather than cause the degradation thereof.

While applicant does not intend to be bound by or to any particular theory, both cysteine and cystine are naturally occurring amino acids in keratin and therefore it is believed that extended exposure of the hair to compositions of the present invention comprising cysteine will tend to replenish these components of the hair. It will also be appreciated by those skilled in the art that very short application periods are also within the scope of the present invention. That is, a very short application period may be desirable when only a modest modification of the natural hair configuration is to be achieved. Accordingly, all application periods are within the scope of the present invention. Applicants have found, however, that based primarily upon convenience considerations, it is preferred to use the following application periods according to the following approximate hair types:

| Hair Type | Approximate Application Period-Minutes |
| --- | --- |
| Fine Hair | 10 to 12 |
| Medium Hair | 15 to 20 |
| Coarse Hair | 20 to 30 |

Another step according to the methods of the present invention comprises placing the hair in the desired configuration. Many particular techniques are well known and available in the art for placing the hair in a variety of different configurations. Although the placing step of the present invention may take place either before, during or after the application period, it is generally preferred practice when straightening kinky or curly hair to place the hair in the desired configuration only after the application period has expired. That is, the hair will generally not be manipulated during the application period. When the present invention is used in the treatment of hair having a naturally straight configuration, however, it is generally preferred that the hair be placed in the modified configuration either before or during the application of the softening composition of the present invention. It is believed that the details of the procedures used in any particular case to achieve the desired reconfiguration of the hair will be available and well known to those skilled in the art. In applications requiring curling or waving naturally straight hair, for example, it is anticipated that the methods of the present invention will include coiling or wrapping the hair around curlers or rods after the softening agent has been applied.

The methods of the present invention also include testing the effectiveness of the softening process. In certain preferred embodiments, especially those embodiments for the straightening of kinky or curly hair, the testing step of the present invention includes running a fine tooth comb through the hair and observing the resiliency of the hair. If the comb moves through the hair with the desired degree of resistance, this is an indication that the softening process has had the desired degree of effectiveness. Depending upon the particular hair type, the extent of desired straightening, and other factors, this step may last a few seconds to several minutes.

According to a preferred aspect of the present invention, the methods of the present invention further include the step of oxidizing the hair which has received the softening composition and which has been placed in the new configuration. This oxidation step can comprise exposing the hair to air or oxygen. In certain other preferred embodiments, the hair is oxidized by contacting it with a chemical oxidizing agent or neutralizer. The oxidization step of the present invention "quenches" the activity of the softening composition. That is, by exposing the softening solution to oxidation, the capacity of the composition to soften the hair is reduced or eliminated. In this way, the precise amount of softening required can be controlled. The oxidation step also aids in the replacement of the disulfide cystine bonds which help give the hair its shape. As discussed earlier, application of the softening composition causes cleavage of these disulfide bonds and, on a macroscopic scale, renders the hair relatively malleable. While not intending to be bound by or to any particular theory, applicant believes that such malleability occurs because at least a portion of the individual protein chains which make up the hair are "decoupled" and allowed to more easily move or slide relative to one another when the disulfide bonds are broken. When the hair is thus subject to the stress caused by placing the hair in the desired configuration, this stress is relieved by the movement of the individual protein chains with respect to one another. The oxidation step according to the methods of the present invention allows such disulfide bonds to be reestablished, thus effecting a permanent reconfiguration of the hair. Standard neutralizing agents are available and well known in the art and the use of all such neutralizing agents are accordingly within the scope of the present invention. Applicant has found, however, that it is preferred to select neutralizing agents from the group consisting of hydrogen peroxides and metal bromate salts, preferably potassium and sodium bromates.

Other well known hair treatment steps may be preferably used in conjunction with the method steps described above. For example, in certain preferred embodiments, the hair is shampooed prior to application of the present invention. Shampooing in this manner removes fatty acids and oils from the hair and allows enhanced penetration of the softening composition. In a like manner, it may also be preferred to condition the hair prior to the application of the softening composition. In certain embodiments, it is also preferred that the hair be rinsed with tepid water after the application period has expired. In general, the solution which is rinsed from the hair will become clear when the rinsing step is complete. More specifically, the rinsing step is expected to last approximately five minutes. In an analogous manner, it is preferred that the hair is also rinsed after the neutralization step is complete. In order to improve the longevity of the curling and straightening process, applicants have also found that it may be desirable to spray the hair after neutralization with an ammonium sulfate solution.

While many techniques are known and available for effectively producing compositions of the present invention, applicant has found that certain preparation methods are preferred for compositions in which the active shaping compound comprises cysteine in major proportion. In particular, it is preferred that cysteine be introduced into solution in the form of hydrated L-cysteine hydrochloride since such material is readily available and contains a relatively precisely known number of milliequivalents of thiol per gram. Due to the acidic nature of hydrated L-cysteine hydrochloride in solution, however, it is preferred that a metal hydroxide be added to the solution during preparation to neutralize the acid component of the L-cysteine hydrochloride. For like reason, it is preferred to add a metal hydroxide to neutralize the acid component when dissolving the cysteamine hydrochloride. Accordingly, it is preferred that potassium or sodium hydroxide be added to the solution in an amount sufficient to provide the required number of milliequivalents of hydroxide to neutralize the acid component of the L-cysteine hydrochloride. In the methods of the present invention for preparing the softening compositions thereof, it is also preferred to introduce a standard anti-oxidant into solution during the preparation process. Although such anti-oxidants are not generally effective for stabilizing the solution, they are beneficial in that they act as scavengers for the oxygen which is introduced into the solution during the preparation process. Other preferred aspects of the preparation methods according to the present invention are disclosed in the examples which follow.

EXAMPLE 1

To a clean, disinfected tank equipped with a mixer, are added 5.5401 pounds of deionized water and then, while mixing, 0.455 pounds of sucrose. Stirring is continued until all the sucrose is dissolved. Then, while mixing, 0.91 pounds of Dequest 2016 (a sodium aminotrimethylene phosphonate chelating agent) is added, followed by 0.7826 pounds of 28% ammonium hydroxide and 0.0910 pounds of Thioset M (a 50% solution of monoethanolamine sulfate) and then 0.6916 pounds of anhydrous L-cysteine hydrochloride. Stirring is continued until complete solution is achieved; then 1.0374 pounds of cysteamine hydrochloride and 0.0018 pounds of sodium bisulfite are added and stirring continued until complete solution is achieved. In a separate stainless steel container, 0.364 pounds of Lipicol L-23 surfactant (Lauryth 23) is heated to 50° C. Then the fragrance is added while mixing is continued until a clear pre-mix solution of fragrance is obtained. Then the pre-mix solution of fragrance is added to the tank and stirring continued for 30 minutes after complete solution is achieved. The foregoing ingredients and their weight percentage of the total composition are listed in Table I below.

The resulting solution is clear, has a pH in the range of 8.35–8.55 at a temperature of about 25° C., an alkali content of about 0.90 to 1.10% by weight and a thio (SH) content of about 1.5 to about 1.7% by weight.

TABLE I

| Description | Quantity (LB) | % By Weight |
| --- | --- | --- |
| DI Water In. | 5.5401 | 60.88021 |
| Sucrose (sugar) | .4550 | 5.00000 |
| Dequest 2016 | .0910 | 1.00000 |
| Aqua Ammonia/Ammonia/NH$_4$OH | .7826 | 8.60000 |
| Thioset M | .0910 | 1.00000 |
| L-Cysteine HCl Anhydrous | .6916 | 7.60000 |
| Cysteamine HCl | 1.0374 | 11.40000 |
| Sodium Bisulfite Ar Grade | .0018 | 0.01978 |
| Lipicol L-23 | .3640 | 4.00000 |
| Frag #128-760 | .0455 | 0.50000 |

EXAMPLE 2

To a clean, disinfected tank equipped with a mixer, are added 5.9230 pounds of deionized water and then, while mixing, 0.445 pounds of sucrose. Stirring is continued until all the sucrose is dissolved. Then, while mixing, 0.089 pounds of Dequest 2016 is added, followed by 0.6764 pounds of 28% ammonium hydroxide and 0.0890 pounds of Thioset M and then 0.4477 pounds of anhydrous L-cysteine hydrochloride. Stirring is continued until complete solution is achieved; then 0.8277 pounds of cysteamine hydrochloride and 0.0018 pounds of sodium bisulfite are added and stirring continued until complete solution is achieved. In a separate stainless steel container, 0.356 pounds of Lipicol L-23 surfactant (Lauryth 23) is heated to 50° C. Then the fragrance is added while mixing is continued until a clear pre-mix solution of fragrance is obtained. Then the pre-mix solution of fragrance is added to the tank and stirring continued for 30 minutes after complete solution is achieved. The foregoing ingredients and their weight percentage of the total composition are listed in Table II below.

The resulting solution is clear, has a pH in the range of 8.65–8.85 at a temperature of about 25° C., an alkali content of about 1.0 to 1.10% by weight and a thio (SH) content of about 1.2 to about 1.3% by weight.

TABLE II

| Description | Quantity (LB) | % By Weight |
| --- | --- | --- |
| DI Water In. | 5.9230 | 66.54981 |
| Sucrose (sugar) | .4450 | 4.99994 |
| Dequest 2016 | .0890 | 0.99998 |
| Aqua Ammonia/Ammonia/ NH₄OH | .6764 | 7.59991 |
| Thioset M | .0890 | 0.99998 |
| L-Cysteine HCl Anhydrous | .4477 | 5.03028 |
| Cysteamine HCl | .8277 | 9.29989 |
| Sodium Bisulfite Ar Grade | .0018 | 0.02022 |
| Lipicol L-23 | .3560 | 3.99995 |
| Frag #128-760 | .0445 | 0.49999 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and that it will be understood that variations can be made without departing from the spirit and scope of the invention.

What is claimed is:

1. A method of modifying the natural conformation of hair containing cystine to cause the hair to maintain a new conformation, said method comprising:
   (a) applying a softening composition to the hair for reductively cleaving at least a portion of the sulfur-sulfur bonds in the cystine, said softening composition comprising an aqueous solution consisting essentially of:
      (i) from about 5 to about 20 percent by weight of said composition of cysteine;
      (ii) from about 5 to about 20 percent by weight of said composition of cysteamine; and
      (iii) from about 3 to about 20 percent by weight of said composition of sucrose, said aqueous solution having a pH of about 5 to about 13 component (i) plus component (ii) together comprising from about 10 to about 25 percent by weight of said composition;
   (b) stressing the hair by positioning the hair in the new conformation;
   (c) substantially removing said softening composition from the hair by rinsing with water; and
   (d) treating the rinsed hair with an oxidizing agent while the hair is in said new conformation.

2. The method of claim 1 wherein said oxidizing agent consists essentially of hydrogen peroxide.

3. The method of claim 1 wherein said cysteine reductively cleaves at least a portion of the cystine disulphide bonds of hair.

4. A composition for increasing the malleability of hair, said composition comprising an aqueous solution which consists essentially of
   (i) from about 5 to about 20 percent by weight of said composition of cysteine;
   (ii) from about 5 to about 20 percent by weight of said composition of cysteamine; and
   (iii) from about 3 to about 20 percent by weight of said composition of sucrose, said aqueous solution having a pH of about 5 to about 13, component (i) plus component (ii) together comprising from about 10 to about 25 percent by weight of said composition.

5. The composition of claim 4 which has a pH of from about 7 to about 11.

6. The composition of claim 4 which comprises from about 3 weight percent to about 15 weight percent of sucrose.

7. The composition of claim 4 which comprises from about 10 to about 15 percent by weight of sucrose.

8. The composition of claim 4 wherein the weight ratio of cysteine to sucrose is from about 2:1 to about 8:1.

9. The composition of claim 4 further comprising a carrier for said cysteine, said cysteamine and said sucrose.

10. The composition of claim 9 wherein said carrier comprises a continuous water phase and a disperse oil phase, said sucrose and said cysteine being substantially dispersed or dissolved in said water phase.

* * * * *